(12) United States Patent
Steinman et al.

(10) Patent No.: US 8,563,308 B2
(45) Date of Patent: Oct. 22, 2013

(54) CULTURE-EXPANDED T SUPPRESSOR CELLS AND METHODS OF USE THEREOF

(75) Inventors: Ralph M. Steinman, Westport, CT (US); Kristin Tarbell, Bethesda, MD (US); Sayuri Yamazaki, New York, NY (US)

(73) Assignee: The Rockefeller University, New York, NY (US)

( * ) Notice: Subject to any disclaimer, the term of this patent is extended or adjusted under 35 U.S.C. 154(b) by 511 days.

(21) Appl. No.: 11/783,752

(22) Filed: Apr. 11, 2007

(65) Prior Publication Data

US 2008/0175830 A1    Jul. 24, 2008

Related U.S. Application Data

(63) Continuation-in-part of application No. 11/074,925, filed on Mar. 9, 2005, now abandoned.

(60) Provisional application No. 60/551,354, filed on Mar. 10, 2004.

(51) Int. Cl.
*C12N 5/071* (2010.01)
*C12N 5/00* (2006.01)
*C12N 5/02* (2006.01)

(52) U.S. Cl.
USPC .................. 435/372.3; 435/377; 435/373

(58) Field of Classification Search
None
See application file for complete search history.

(56) References Cited

U.S. PATENT DOCUMENTS

2003/0096314 A1* 5/2003 Steinman et al. ............. 435/7.2
2005/0186207 A1* 8/2005 Bluestone et al. .......... 424/144.1
2006/0067912 A1* 3/2006 Horwitz ....................... 424/85.2
2006/0115899 A1* 6/2006 Buckner et al. ............... 435/372

OTHER PUBLICATIONS

Siena et al., 1997, The Oncologist, vol. 2: 65-69.*
Dai et al., 2005, J. Immunol. vol. 175: 3621-3627.*
Maron et al., 1999, J. Autoimmun. vol. 12: 251-258.*
Game et al., J Am Soc Nephrol vol. 14: 1652-1661.*
Chen et al., Dec. 2003, J. Exp. Med. vol. 198: 1875-1886.*
Jonuleit et al., 2000, J. Exp. Med. vol. 192: 1213-1222.*
Kretschmer et al., 2005, Nat. Immunol. vol. 6: 1219-1227.*
Tarbell et al., 2004. J. Exp. Med. VOl. 199: 1467-1477.*

* cited by examiner

*Primary Examiner* — Amy Juedes
(74) *Attorney, Agent, or Firm* — Fox Rothschild LLP; Gerard P. Norton; J. Jimmy Hao (57) ABSTRACT

This invention relates to culture-expanded T suppressor cells derived from $CD25^-CD4^+$ T cells, and their use in modulating immune responses. This invention provides methods of producing culture-expanded T suppressor cells, which are antigen specific, and their use in modulating autoimmune diseases and transplantation rejection.

13 Claims, 6 Drawing Sheets

CULTURE-EXPANDED T SUPPRESSOR CELLS AND METHODS OF USE THEREOF

CROSS-REFERENCE TO RELATED APPLICATIONS

This application is a continuation-in-part of U.S. patent application Ser. No. 11/074,925, filed Mar. 9, 2005 now abandoned, which claims the benefit of U.S. Provisional Application Ser. No. 60/551,354, filed Mar. 10, 2004, which is hereby incorporated by reference in its entirety.

STATEMENT AS TO FEDERALLY SPONSORED RESEARCH

This invention was conducted with U.S. Government support under National Institutes of Health grant Number NIH 5 P01 AI 51573. The government has certain rights in the invention.

FIELD OF THE INVENTION

This invention relates to culture-expanded T suppressor cells and their use in modulating immune responses. This invention provides facile methods of producing culture-expanded T suppressor cells from a more abundant yet quiescent population of naïve T cells, which are antigen specific, and their use in modulating complex autoimmune diseases.

BACKGROUND OF THE INVENTION

Tolerance mechanisms for autoreactive T cells can be of "intrinsic" and "extrinsic" varieties. Intrinsic mechanisms include deletion and anergy of self-reactive T cells, while extrinsic mechanisms include different regulatory T cells (Tregs) that suppress other self-reactive T cells. One type of extrinsic suppressor is the $CD25^+$ $CD4^+$ T cell, which constitutes 5-10% of $CD4^+$ peripheral T cells. These are produced in the thymus and maintain tolerance to self-antigens, as well as play a role in other immune responses, such as in infection, transplants and graft versus host disease. In autoimmune diseases such as diabetes, considerable effort has been focused on expanding the small numbers of such Tregs. Expansion of this population using methods such as, for example, employing dendritic cells presenting antigenic peptide or a T cell receptor cross-linking agent, are described in U.S. patent application Ser. No. 11/074,925, filed Mar. 9, 2005.

However, the $CD25^-$ $CD4^+$ T cell population is a more abundant population with the potential to differentiate into Tregs. While it is known that this T cell population can be differentiated into $CD4^+CD25^+$ T regs by stimulation with mitogenic antibodies in the presence of TGF-$\beta$1, it is not known whether these induced cells are functionally identical to Tregs that develop in the thymus. Such "induced T regs" with islet specificity can prevent diabetes in lymphopoietic models, but their ability to induce tolerance at late pathogenic stages of autoimmunity, such as in already-diabetic NOD mice, has not been fully addressed.

In T cell population, the transcription factor, FoxP3, is important for $CD25^+$ $CD4^+$ T cell suppressor activity, and children who are born with defective FoxP3 rapidly develop autoimmunity, such as, for example, autoimmune diabetes. Models for the study of autoimmunity have played a critical role in both the understanding of the pathogenesis, and the devising of therapeutic strategies for these diseases. In a mouse model of autoimmune diabetes, the non-obese diabetic (NOD) mice, for example, $CD25^+$ $CD4^+$ regulatory T cells inhibit diabetes development, making this extrinsic tolerance mechanism an attractive target to develop antigen-specific therapies for autoimmune disease. In an experimental model of multiple sclerosis mediated by transgenic T cells specific to myelin basic protein, $CD25^+$ $CD4^+$ T cells specific for this antigen showed better suppression of disease than $CD25^+$ $CD4^+$ T cells with T cell receptors (TCRs) specific for other antigens. These findings suggest a role for antigen-specific $CD25^+$ $CD4^+$ T cells in suppressing autoimmunity.

Means for expanding $CD25^+$ $CD4^+$ T cells without the use of mitogenic stimuli to differentiate T regs has numerous potential therapeutic advantages.

SUMMARY OF THE INVENTION

In one embodiment, an isolated, culture-expanded $CD25^+$ $CD4^+$ T suppressor cell population is provided, wherein said population is prepared by the process of exposing $CD25^-$ $CD4^+$ T cells to dendritic cells, antigen and TGF-$\beta$1. In another embodiment the $CD25^-CD4^+$ T cells are Foxp3-. In another embodiment, the dendritic cells are presenting the antigen or a peptide thereof. In yet another embodiment, the $CD25^+CD4^+$ population further expresses Foxp3 on its surface. In a further embodiment, the $CD25^+CD4^+$ population is antigen specific. In yet a further embodiment, the antigen is a self-antigen, or a derivative thereof, such as but no limited to a self antigen is expressed on pancreatic beta cells, or a transplantation antigen.

In another embodiment, a method is provided for producing an isolated, culture-expanded $CD25^+CD4^+$ T suppressor cell population, comprising the steps of (a) contacting a population of $CD25^-CD4^+$ T cells with dendritic cells; an antigen selected from the group consisting of an antigenic peptide, an antigenic protein, and a derivative thereof; and TGF-$\beta$1, for a period of time resulting in antigen-specific $CD25^+CD4^+$ T cell differentiation and expansion; and (b) isolating the expanded $CD25^+CD4^+$ T cells obtained in (a). In another embodiment, the dendritic cells are presenting the antigen or a peptide thereof. In yet another embodiment, the $CD25^+$ $CD4^+$ population further expresses Foxp3 on its surface. In a further embodiment, the $CD25^+CD4^+$ population is antigen specific. In yet a further embodiment, the antigen is a self-antigen, or a derivative thereof, such as but no limited to a self antigen is expressed on pancreatic beta cells, or a transplantation antigen.

In still another embodiment, a method is provided for delaying onset, reducing incidence, suppressing or treating autoimmunity, an autoimmune disease or an autoimmune disorder in a subject, comprising the steps of (a) contacting a population of $CD25^-CD4^+$ T cells with dendritic cells; an antigen selected from the group consisting of an antigenic peptide, an antigenic protein, and a derivative thereof; and TGF-$\beta$1, for a period of time resulting in antigen-specific $CD25^+CD4^+$ T cell differentiation and expansion; and (b) administering the expanded $CD25^+CD4^+$ T cells obtained in (a) to a subject. The dendritic cells, in one embodiment, are presenting the antigen or a peptide thereof. In another embodiment, the dendritic cells are isolated from said subject. In another embodiment, the $CD25^-CD4^+$ T cells are isolated from said subject. In another embodiment, the T cells are syngeneic or allogeneic, with respect to said dendritic cells and said subject. The $CD25^+CD4^+$ T suppressor cell population, in another embodiment, further expresses Foxp3 on its surface. In another embodiment, the $CD25^+CD4^+$ T suppressor cell population is antigen specific.

In other embodiments, the antigen is a self-antigen, or a derivative thereof, such as but not limited to a self antigen is expressed on pancreatic beta cells, or a transplantation antigen. In still other embodiment, the expanded CD25$^+$CD4$^+$ T suppressor cell population suppresses an autoimmune response, such as against rheumatoid arthritis or against an inflammatory response, an allergic response, or downmodulates an immune response. The immune response can be, in other embodiment, graft versus host disease or host versus graft disease. In still other embodiments, the dendritic cells are isolated from a subject suffering from an autoimmune disease or disorder, such as an individual with a allergic response, a recipient of a transplant, or the antigenic peptide or antigenic protein or derivative thereof is associated with said autoimmune disease or disorder. In one embodiment, the autoimmune disease or disorder is type I diabetes. In another embodiment, the antigenic peptide or protein is expressed in pancreatic beta cells. In another embodiment, the antigenic peptide is a BDC mimetope.

In another embodiment, a method is provided for downmodulating an immune response in a subject, comprising the steps of (a) contacting a population of CD25$^-$CD4$^+$ T cells with dendritic cells; an antigen selected from the group consisting of an antigenic peptide, an antigenic protein, and a derivative thereof; and TGF-β1, for a period of time resulting in antigen-specific CD25$^+$CD4$^+$ T cell differentiation and expansion; and (b) administering the expanded CD25$^+$CD4$^+$ T cells obtained in (a) to a subject. The dendritic cells, in one embodiment, are presenting the antigen or a peptide thereof. In another embodiment, the dendritic cells are isolated from said subject. In another embodiment, the CD25$^-$CD4$^+$ T cells are isolated from said subject. In another embodiment, the T cells are syngeneic or allogeneic, with respect to said dendritic cells and said subject. The CD25$^+$CD4$^+$ T suppressor cell population, in another embodiment, further expresses Foxp3 on its surface. In another embodiment, the CD25$^+$CD4$^+$ T suppressor cell population is antigen specific.

In other embodiments, the antigen is a self-antigen, or a derivative thereof, such as but not limited to a self antigen is expressed on pancreatic beta cells, or a transplantation antigen. In still other embodiment, the expanded CD25$^+$CD4$^+$ T suppressor cell population suppresses an autoimmune response, such as against rheumatoid arthritis or against an inflammatory response, an allergic response, or downmodulates an immune response. The immune response can be, in other embodiment, graft versus host disease or host versus graft disease. In still other embodiments, the dendritic cells are isolated from a subject suffering from an autoimmune disease or disorder, such as an individual with a allergic response, a recipient of a transplant, or the antigenic peptide or antigenic protein or derivative thereof is associated with said autoimmune disease or disorder. In one embodiment, the autoimmune disease or disorder is type I diabetes. In another embodiment, the antigenic peptide or protein is expressed in pancreatic beta cells. In another embodiment, the antigenic peptide is a BDC mimetope.

In another embodiment, a method is provided for delaying onset, reducing incidence, suppressing or treating autoimmunity, an autoimmune disease or autoimmune disorder in a subject, comprising the step of contacting a dendritic cell population in vivo with an antigenic peptide or protein associated with an autoimmune response in said subject, or a derivative thereof, and TGF-β1 for a period of time whereby said dendritic cells contact CD25$^-$CD4$^+$ T cells in said subject, inducing and stimulating antigen-specific induction and expansion into CD25$^+$CD4$^+$ T cells in said subject, wherein expanded CD25$^+$CD4$^+$ T cells suppress an autoimmune response in said subject, thereby delaying onset, reducing incidence, suppressing or treating autoimmunity, an autoimmune disease or an autoimmune disorder.

In the aspects of the invention mentioned above, in one embodiment the dendritic cells can be modified to express the aforementioned antigen. In other embodiments, the dendritic cells can be modified or treated to express TGF-β1.

BRIEF DESCRIPTION OF THE DRAWINGS

FIG. 1 shows that splenic dendritic cells (DCs) efficiently induce Foxp3 expression from naïve CD4$^+$CD25$^-$ T cells. (A) Cell surface expression of CD40, CD86, and MHC class II (I-A$^{g7}$) of freshly isolated NOD splenic CD11c$^+$ DCs. (B) Foxp3 expression by precultured sorted CD4$^+$CD25$^-$CD62L$^+$ BDC2.5 T cells and induction in T cells after culture with or without 2 ng/ml TGF-β1 on day 6 of culture. Expression of CD62L by precultured CD4$^+$CD25$^-$ BDC2.5 T cells is also shown. (C) Time-course of induction of CD4$^+$CD25$^+$Foxp3$^+$ BDC2.5 T cells from naïve CD4$^+$CD25$^-$Foxp3$^-$ BDC2.5 T cells in the presence of 2 ng/ml TGF-β1. (Upper) Total number of Foxp3$^+$ T cells per well. (Lower) Percentages of Foxp3$^+$ T cells determined by intracellular staining on days 2, 3, 4, 5, 6, and 10 of DC-T cultures. The isotype control for day 3 is shown. (D) Quantification of Foxp3 mRNA by real-time RT-PCR. Samples were prepared from enriched CD25$^+$ fractions of the resulting T cells from cocultures with or without 2 ng/ml TGF-β1 or freshly isolated CD4$^+$CD25$^+$ and CD4$^+$CD25$^-$ BDC2.5 T cells. Values were standardized by 18s RNA and expressed as fold of increase compared with precultured freshly isolated CD4$^+$CD25$^-$ cells. (E) Dose-response of TGF-β1 determined on day 6 of DC-T cocultures at indicated concentrations of TGF-β1. The isotype control for the 0.01 ng/ml dose is shown. All results are representative of two to four separate experiments.

DETAILED DESCRIPTION OF THE PRESENT INVENTION

Naive CD4⁺CD25⁻ T cells comprise an abundant and population of potential T reg cells (suppressor T cells). If induced and expanded in vitro, ex vivo or in vivo under the proper conditions or with the proper treatments, this population represents a significantly prevalent and practical source of potential antigen-specific suppressors clinically useful for addressing immune-mediated diseases including autoimmune diseases such as diabetes, as well as induction of tolerance in, for example, transplantation immunity.

Thus, in one embodiment, induction and differentiation of CD4⁺CD25⁻ T cells into T suppressor cells is achieved by exposure of naive CD4⁺CD25⁻ T cells to dendritic cells pulsed with or exposed at least to disease-specific antigen or peptide, in the presence of TGF-β1. In another embodiment, the disease specific antigen is an autoimmune disease antigen. In another embodiment, the disease specific antigen is a transplant antigen. In another embodiment, the method is carried out in vitro. In still another embodiment, the method is carried out ex vivo. In yet another embodiment, the method is carried out in vivo.

As will be described in greater detail below, in other embodiments, a culture-expanded population of CD25⁺CD4⁺ T suppressor cells is provided by carrying out the aforementioned methods. In another embodiment, the population is used for suppressing or downregulating an immune response or treating an autoimmune disease or disorder in a subject. Such methods in one embodiment can be carried out ex vivo. In yet other embodiments, the induction and expansion of the aforementioned population can be achieved in vivo.

As will be seen in the Examples below, the ability of dendritic cells (DCs) from NOD mice to induce islet antigen-specific CD4⁺CD25⁺Foxp3⁺ T cells from naive CD4⁺CD25⁻Foxp3⁻ T cells was demonstrated. By using T cells from BDC2.5 mice, a well described diabetogenic CD4⁺ TCR transgenic system, DCs, together with specific peptide and TGF-β1, induced CD4⁺CD25⁺Foxp3⁺ T cells that maintain islet-antigen specificity. The stimulation with DCs and TGF-β1 results in T cells that have high levels of Foxp3 as well as specific TCR expression, and these T cells are able to suppress proliferation and cytokine responses in vitro. Importantly, the DC+TGF-β1-induced CD4⁺CD25⁺Foxp3⁺ T cells also are potent suppressors of ongoing autoimmune diabetes in vivo and provide significant protection for syngeneic islet grafts in diabetic mice from established autoimmune destruction.

The generation of T suppressor cells and various methods of invention are applicable generally to the suppression of the immune response and treatment of autoimmune diseases and disorders. The methods are not limited to any particular antigen, disease, or expression of cell surface markers on CD25⁺CD4⁺ T suppressor cells induced and expanded by following the teachings herein. By selection of at least one antigen or protein for which suppression is desired, by following the teaching herein, a useful population of T suppressor cells is generated in vitro, ex vivo or in vivo.

Thus, in one embodiment is provided an isolated culture-expanded T suppressor cell population, which expresses CD25 and CD4 on its cell surface, methods of producing the same, and methods of use thereof, wherein the CD25⁺ CD4⁺ T cells are produced by the process of exposing CD4⁺CD25⁻ cells to dendritic cells, antigen and TGF-β1. In another embodiment, the process comprises exposing CD4⁺CD25⁻ cells to dendritic cells presenting antigen, and TGF-β1. As will be described in more detail below, in certain embodiments the dendritic cells can be modified to express antigen, and in other embodiments, to express or be induced to express TGF-β1.

In one embodiment, the phrase "T suppressor cell" or "suppressor T cell", or "regulatory T cell", refers to a T cell population that inhibits or prevents the activation, or in another embodiment, the effector function, of another T lymphocyte. In one embodiment, the T suppressors are a homogenous population, or in another embodiment, a heterogeneous population.

The T suppressor cells induced by the processes of this invention express CD25 and CD4 on their cell surface. In another embodiment, the T suppressor cells may express Foxp3. In another embodiment, the T suppressor cells may express CTLA-4, or in another embodiment, GITR. In one embodiment, the T suppressor cells may be classified as CTLA-4$^{high}$ expressors, or in another embodiment, the T suppressor cells may be classified as GITR$^{high}$, or in another embodiment, a combination thereof. In another embodiment, the T suppressor cells of this invention are CD69⁻. In another embodiment, the T suppressor cells of this invention are CD62L$^{hi}$, CD45RB$^{lo}$, CD45RO$^{hi}$, CD45RA⁻, $\alpha_E\beta_7$ integrin expressors, or any combination thereof. It is to be understood that the isolated culture-expanded T suppressor cells of this invention may express in addition to CD25 and CD4 any number or combination of cell surface markers, as described herein, and as is well known in the art, and are to be considered as part of this invention.

In one embodiment, the T suppressor cells of this invention express the CD62L antigen, which in one embodiment, is a 74 kDa glycoprotein, and in another embodiment, is a member of the selectin family of cell surface molecules. In another embodiment, the phrase "CD62L" may also be referred to as "L-selectin", "LECAM-1", or "LAM-1", all of which are to be considered synonymous herein. CD62L binds a series of glycoproteins, in other embodiments, including CD34, Gly-CAM-1 and MAdCAM-1. CD62L is important, in another embodiment, for homing of the lymphocytes via the high endothelial venules to peripheral lymph nodes and Peyer's patches, where in another embodiment, they may carry out their effector function, for example, and in one embodiment, suppression of autoimmune responses. The CD62L antigen also contributes, in another embodiment, to the recruitment of leukocytes from the blood to areas of inflammation, and in another embodiment, recruited cells may thereby be induced to become suppressor cells.

In one embodiment, the T suppressor cells of this invention are obtained by positive selection for expression of CD4 and CD25, and in another embodiment, the T suppressor cells may also be selected for the absence of CD45RA expression, i.e. negative selection procedures, as are well known in the art. In another embodiment, other markers can be used to further separate subpopulations of the T suppressor cells, including CD69, CCR6, CD30, CTLA-4, CD62L, CD45RB, CD45RO, Foxp3, or a combination thereof.

In one embodiment, the naïve CD25$^-$CD4$^+$ T cells of this invention may be obtained from in vivo sources, such as, for example, peripheral blood, leukopheresis blood product, apheresis blood product, peripheral lymph nodes, gut associated lymphoid tissue, spleen, thymus, cord blood, mesenteric lymph nodes, liver, sites of immunologic lesions, e.g. synovial fluid, pancreas, cerebrospinal fluid, tumor samples, granulomatous tissue, or any other source where such cells may be obtained. In one embodiment, the T cells are obtained from human sources, which may be, in another embodiment, from human fetal, neonatal, child, or adult sources. In another embodiment, the T cells of this invention may be obtained from animal sources, such as, for example, porcine or simian, or any other animal of interest. In another embodiment, the T cells of this invention may be obtained from subjects that are normal, or in another embodiment, diseased, or in another embodiment, susceptible to a disease of interest.

In one embodiment, the T cells and/or dendritic cells, as described further hereinbelow, of this invention are isolated from tissue, and, in another embodiment, an appropriate solution may be used for dispersion or suspension, toward this end. In another embodiment, T cells and/or dendritic cells, as described further hereinbelow, of this invention may be cultured in solution.

Such a solution may be, in another embodiment, a balanced salt solution, such as normal saline, PBS, or Hank's balanced salt solution, or others, each of which represents another embodiment of this invention. The solution may be supplemented, in other embodiments, with fetal calf serum, bovine serum albumin (BSA), normal goat serum, or other naturally occurring factors, and, in another embodiment, may be supplied in conjunction with an acceptable buffer. The buffer may be, in other embodiments, HEPES, phosphate buffers, lactate buffers, or the like, as will be known to one skilled in the art.

In another embodiment, the solution in which the T cells or dendritic cells of this invention may be induced, differentiated or expanded is in medium is which is serum-free, which may be, in another embodiment, commercially available, such as, for example, animal protein-free base media such as X-VIVO 10™ or X-VIVO 15™ (BioWhittaker, Walkersville, Md.), Hematopoietic Stem Cell-SFM media (GibcoBRL, Grand Island, N.Y.) or any formulation which promotes or sustains cell viability. Serum-free media used, may, in another embodiment, be as those described in the following patent documents: WO 95/00632; U.S. Pat. No. 5,405,772; PCT US94/09622. The serum-free base medium may, in another embodiment, contain clinical grade bovine serum albumin, which may be, in another embodiment, at a concentration of about 0.5-5%, or, in another embodiment, about 1.0% (w/v). Clinical grade albumin derived from human serum, such as Buminate® (Baxter Hyland, Glendale, Calif.), may be used, in another embodiment.

In another embodiment, the CD25$^-$CD4 T cells of this invention may be isolated or separated via affinity-based separation methods. Techniques for affinity separation may include, in other embodiments, magnetic separation, using antibody-coated magnetic beads, affinity chromatography, cytotoxic agents joined to a monoclonal antibody or use in conjunction with a monoclonal antibody, for example, complement and cytotoxins, and "panning" with an antibody attached to a solid matrix, such as a plate, or any other convenient technique. In other embodiment, separation techniques may also include the use of fluorescence activated cell sorters, which can have varying degrees of sophistication, such as multiple color channels, low angle and obtuse light scattering detecting channels, impedance channels, etc. It is to be understood that any technique, which enables separation of the T cells of this invention may be employed, and is to be considered as part of this invention.

In another embodiment, the affinity reagents employed in the separation methods may be specific receptors or ligands for the cell surface molecules indicated hereinabove. In other embodiments, peptide-MHC antigen and T cell receptor pairs may be used; peptide ligands and receptor; effector and receptor molecules, or others. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

In another embodiment, the antibodies utilized herein may be conjugated to a label, which may, in another embodiment, be used for separation. Labels may include, in other embodiments, magnetic beads, which allow for direct separation, biotin, which may be removed with avidin or streptavidin bound to, for example, a support, fluorochromes, which may be used with a fluorescence activated cell sorter, or the like, to allow for ease of separation, and others, as is well known in the art. Fluorochromes may include, in one embodiment, phycobiliproteins, such as, for example, phycoerythrin, allophycocyanins, fluorescein, Texas red, or combinations thereof. In one embodiment, antibodies are labeled. In one embodiment suppressors can be purified by positive or negative selection.

In one embodiment, cell separations utilizing antibodies will entail the addition of an antibody to a suspension of cells, for a period of time sufficient to bind the available cell surface antigens. The incubation may be for a varied period of time, such as in one embodiment, for 5 minutes, or in another embodiment, 15 minutes, or in another embodiment, 30 minutes. Any length of time which results in specific labeling with the antibody, with minimal non-specific binding is to be considered envisioned for this aspect of the invention.

In another embodiment, the staining intensity of the cells can be monitored by flow cytometry, where lasers detect the quantitative levels of fluorochrome (which is proportional to the amount of cell surface antigen bound by the antibodies). Flow cytometry, or FACS, can also be used, in another embodiment, to separate cell populations based on the intensity of antibody staining, as well as other parameters such as cell size and light scatter.

In another embodiment, the labeled cells are separated based on their expression of CD4 and CD25. In another embodiment, the cells may be further separated based on their expression of Foxp3. The separated cells may be collected in any appropriate medium that maintains cell viability, and may, in another embodiment, comprise a cushion of serum at the bottom of the collection tube.

In another embodiment, the culture containing the induced, differentiated or expanded T cells of this invention may contain cytokines or growth factors to which the cells are responsive. In one embodiment, the cytokines or growth factors promote survival, growth, function, or a combination thereof of the T suppressor cells. Cytokines and growth factors may include, in other embodiment, polypeptides and non-polypeptide factors. In one embodiment, the cytokines may comprise interleukins.

In one embodiment, the isolated culture-expanded T suppressor cell populations of this invention are antigen specific.

In one embodiment, the term "antigen specific" refers to a property of the population such that supply of a particular antigen, or in another embodiment, a fragment of the antigen, results, in one embodiment, in specific suppressor cell proliferation, when presented the antigen, in the context of MHC. In another embodiment, supply of the antigen or fragment thereof, results in suppressor cell production of interleukin 2, or in another embodiment, enhanced expression of the T cell receptor (TCR) on its surface, or in another embodiment, suppressor cell function. In one embodiment, the T suppressor cell population expresses a monoclonal T cell receptor. In another embodiment, the T suppressor cell population expresses polyclonal T cell receptors.

In one embodiment, the T suppressor cells will be of one or more specificities, and may include, in another embodiment, those that recognize a mixture of antigens derived from an antigenic source, such as, for example, in diabetes, where recognition of a pancreatic beta cell line or islet tissue itself may be used to expand the T suppressor cells. In one embodiment suppressors can be purified by positive or negative selection.

In another embodiment, the antigen is a self-antigen. In one embodiment, the term "self-antigen" refers to an antigen that is normally expressed in the body from which the suppressor T cell population is derived. In another embodiment, self-antigen is comparable to one, or, in another embodiment, indistinct from one normally expressed in a body from which the suppressor T cell population is derived, though may not directly correspond to the antigen. In another embodiment, self-antigen refers to an antigen, which when expressed in a body, may result in the education of self-reactive T cells. In one embodiment, self-antigen is expressed in an organ that is the target of an autoimmune disease. In one embodiment, the self-antigen is expressed in a pancreas, thyroid, connective tissue, kidney, lung, digestive system or nervous system. In another embodiment, self-antigen is expressed on pancreatic beta cells.

In another embodiment, a library of peptides that span an antigenic protein is used in this invention. In one embodiment, the peptides are about 15 amino acids in length, and may, in another embodiment, be staggered every 4 amino acids along the length of the antigenic protein.

Figure 4:
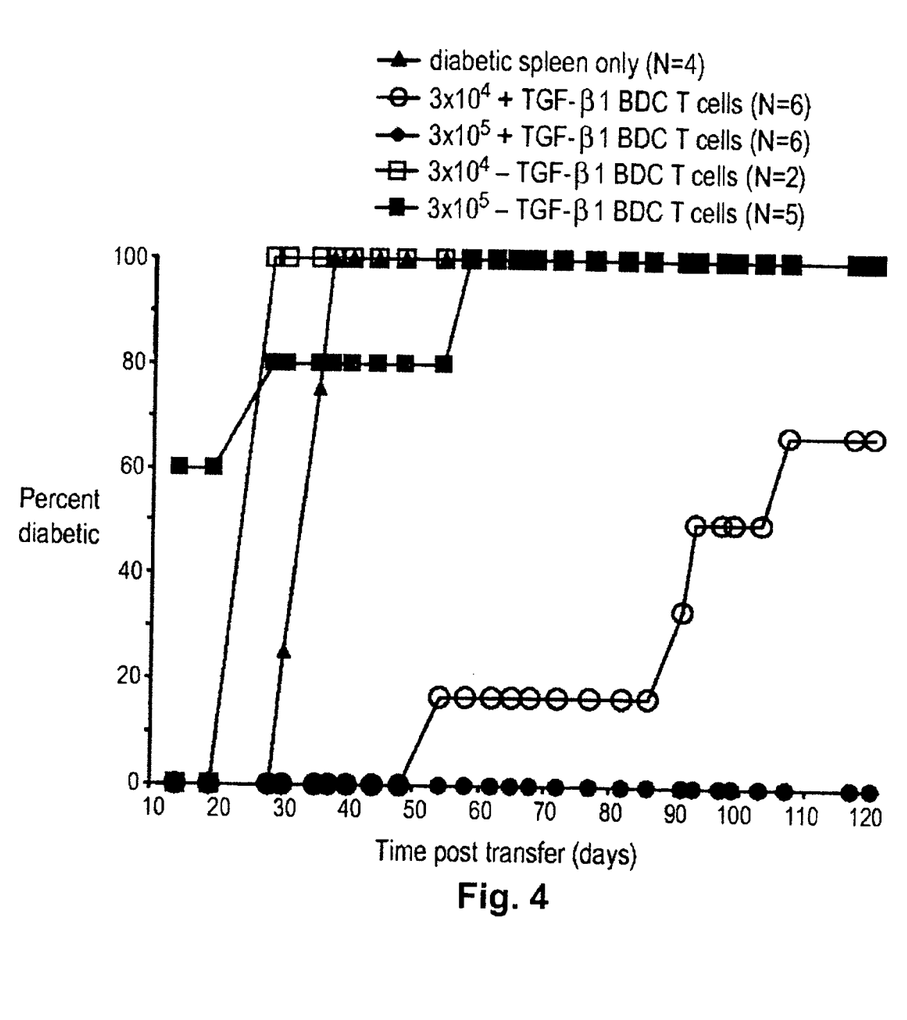
FIG. 4 shows that CD4$^+$CD25$^+$Foxp3$^+$ BDC T cells induced by DCs and TGF-β1 block the development of diabetes in NOD.scid recipients. NOD.scid mice were injected i.v. with 10$^7$ spleen cells from diabetic NOD females with either nothing (red triangles) or the indicated numbers of CD4$^+$CD25$^+$ BDC T cells from cultures with splenic DCs in the presence (+TGF-β1 BDC T, open circles) or absence (−TGF-β1 BDC T, solid squares) of TGF-β1. P<0.0001, control vs. 3×10⁵+TGF-β1 BDC T cells; P<0.0001, control vs. 3×10⁴+TGF-β1 BDC T cells.
Figure 5:
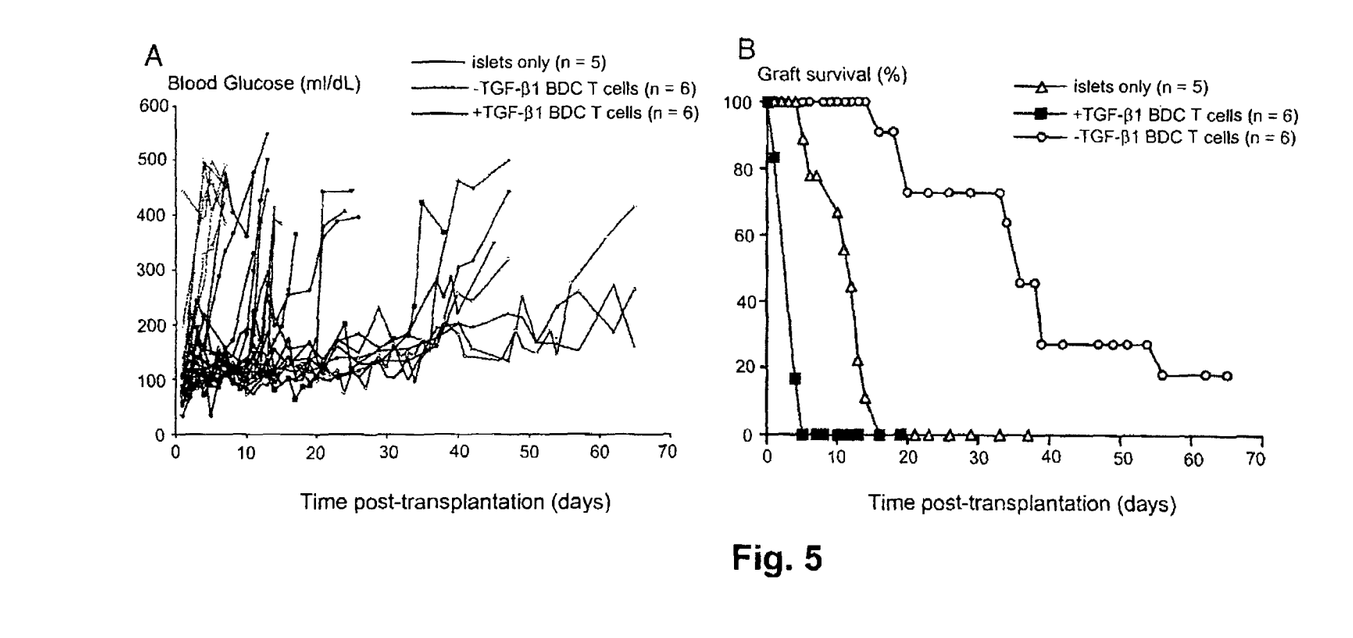
FIG. 5 shows that CD4⁺CD25⁺Foxp3⁺ BDC T cells induced by DCs and TGF-β1 protect syngeneic islet grafts from ongoing autoimmune destruction in spontaneously diabetic NOD recipients. A total of 500 NOD islets were transplanted into kidney subcapsular space either alone or with 3×10⁵+TGF-β1 BDC T cells or −TGF-β1 BDC T cells. Day 0 indicates the day of islet transplantation. Data shown is the summary of graft survival after transplantation for individual mice. P<0.0001 for comparison of graft survival among all three groups; P=0.0069, −TGF-β1 BDC T vs. islets only; P=0.0001, +TGF-β1 BDC T vs. islets only. Data represent the combination of three separate transplant experiments with cells from three separate cultures.

In one embodiment, the isolated culture-expanded T suppressor cell population prepared by the process described herein suppresses an autoimmune response. In one embodiment, the term "autoimmune response" refers to an immune response directed against an auto- or self-antigen. In one embodiment, the autoimmune response is directed to amelioration of rheumatoid arthritis, multiple sclerosis, diabetes mellitus, myasthenia gravis, pernicious anemia, Addison's disease, lupus erythematosus, Reiter's syndrome, atopic dermatitis, psoriasis or Graves disease. In one embodiment, the autoimmune disease caused in the subject is a result of self-reactive T cells, which recognize multiple self-antigens. In one embodiment, the T suppressor cell populations of this invention may be specific for a single self-antigen in a disease where multiple self-antigens are recognized, yet the T suppressor cell population effectively suppresses the autoimmune disease. Such a phenomenon was exemplified herein, for example, in FIG. 4, where beta cell peptide-pulsed DC and TGF-β1-induced $CD25^+$ $CD4^+$ suppressor T cells into NOD mice rendered diabetic with diabetic spleen cells, prevented the development of diabetes, which is a disease wherein autoreactive T cells recognize multiple self-antigens. Furthermore, islet grafts were protected from autoimmune destruction (FIG. 5).

In another embodiment, the antigen may be any molecule recognized by the immune system of the mammal as foreign. For example, the antigen may be any foreign molecule, such as a protein (including a modified protein such as a glycoprotein, a mucoprotein, etc.), a nucleic acid, a carbohydrate, a proteoglycan, a lipid, a mucin molecule, or other similar molecule, including any combination thereof. The antigen may, in another embodiment, be a cell or a part thereof, for example, a cell surface molecule. In another embodiment, the antigen may derive from an infectious virus, bacterium, fungus, or other organism (e.g., protists), or part thereof. These infectious organisms may be active, in one embodiment or inactive, in another embodiment, which may be accomplished, for example, through exposure to heat or removal of at least one protein or gene required for replication of the organism.

In one embodiment, the term "antigen" refers to a protein, or peptide, associated with a particular disease for which the cells of this invention are being used to modulate, or for use in any of the methods of this invention. In one embodiment, the term "antigen" may refer to a synthetically derived molecule, or a naturally derived molecule, which shares sequence homology with an antigen of interest, or structural homology with an antigen of interest, or a combination thereof. In one embodiment, the antigen may be a mimetope.

In another embodiment, isolated culture-expanded T suppressor cell population suppresses an inflammatory response. In one embodiment, the term "inflammatory disorder" refers to any disorder that is, in one embodiment, caused by an "inflammatory response" also referred to, in another embodiment, as "inflammation" or, in another embodiment, whose symptoms include inflammation. By way of example, an inflammatory disorder caused by inflammation may be a septic shock, and an inflammatory disorder whose symptoms include inflammation may be rheumatoid arthritis. The inflammatory disorders of the present invention comprise, in another embodiment, cardiovascular disease, rheumatoid arthritis, multiple sclerosis, Crohn's disease, inflammatory bowel disease, systemic lupus erythematosis, polymyositis, septic shock, graft versus host disease, host versus graft disease, asthma, rhinitis, psoriasis, cachexia associated with cancer, or eczema. In one embodiment, as described hereinabove, the inflammation in the subject may be a result of T cells, which recognize multiple antigens in the subject. In one embodiment, the T suppressor cell populations of this invention may be specific for a single antigen where multiple antigens are recognized, yet the T suppressor cell population effectively suppresses the inflammation in the subject.

In another embodiment, the isolated culture-expanded T suppressor cell populations of this invention suppress an allergic response. In one embodiment, the term "allergic response" refers to an immune system attack against a generally harmless, innocuous antigen or allergen. Allergies may in one embodiment include, but are not limited to, hay fever, asthma, atopic eczema as well as allergies to poison oak and ivy, house dust mites, bee pollen, nuts, shellfish, penicillin or other medications, or any other compound or compounds which induce an allergic response. In one embodiment, multiple allergens elicit an allergic response, and the antigen recognized by the T suppressor cells of this invention may be any antigen thereof.

In another embodiment, the isolated culture-expanded T suppressor cell population downmodulates an immune response. In one embodiment, an immune response to a particular antigen may be beneficial to the host, such as, for example, a response directed against an antigen from a pathogen that has invaded the subject. In one embodiment, such an immune response may be too robust, such that even after the pathogen has been eradicated, or controlled, the immune response is sustained and causes damage to the host, such as, for example, by causing tissue necrosis, in tissue which formerly was infected with the pathogen. In these and other circumstances, the isolated culture-expanded T suppressor cell population may be useful in downmodulating an immune response, such that the host is not compromised in any way by the persistence of such an immune response.

In another embodiment, the immune response, whose downmodulation is desired is host versus graft disease. With the improvement in the efficiency of surgical techniques for transplanting tissues and organs such as skin, kidney, liver, heart, lung, pancreas and bone marrow to subjects, perhaps the principal outstanding problem is the immune response mounted by the recipient to the transplanted allograft or organ, often resulting in rejection. When allogeneic cells or organs are transplanted into a host (i.e., the donor and recipient are different individual from the same species), the host immune system is likely to mount an immune response to foreign antigens in the transplant (host-versus-graft disease) leading to destruction of the transplanted tissue. Accordingly, the isolated culture-expanded T suppressor cell population may be used, in one embodiment, to prevent such rejection of transplanted tissue or organ.

In another embodiment, the immune response, whose downmodulation is desired is graft versus host disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The isolated culture-expanded T suppressor cell population may be used, in one embodiment, to preventing or ameliorating such disease.

It is to be understood that the downmodulation of any immune response, via the use of the isolated culture-expanded T suppressor cell populations of this invention are to be considered as part of this invention, and an embodiment thereof.

In one embodiment, the isolated culture-expanded T suppressor cell populations secrete substances, which mediate the suppressive effects. In one embodiment, the T suppressor cells of this invention mediate bystander suppression, without a need for direct cell contact. In one embodiment, the substances mediating suppression secreted by the T suppressor cell populations of this invention may include IL-10, TGF-$\beta$1, or a combination thereof. The secretion of TGF-$\beta$1 from such cell populations can contribute in a paracrine fashion to the further induction and expansion of the T suppressor cell population from CD25$^-$CD4$^+$ T cells and induction of Foxp3 expression for the desired purposes herein.

In another embodiment, the isolated culture-expanded T suppressor cell populations may be engineered to express substances which when secreted mediate suppressive effects, such as, for example, the cytokines listed hereinabove. In another embodiment, the isolated culture-expanded T suppressor cell populations may be engineered to express particular adhesion molecules, or other targeting molecules, which, when the cells are provided to a subject, facilitate targeting of the T suppressor cell populations to a site of interest. For example, when T suppressor cell activity is desired to downmodulate or prevent an immune response at a mucosal surface, the isolated culture-expanded T suppressor cell populations of this invention may be further engineered to express the $\alpha_e\beta_7$ adhesion molecule, which has been shown to play a role in mucosal homing. The cells can be engineered to express other targeting molecules, such as, for example, an antibody specific for a protein expressed at a particular site in a tissue, or, in another embodiment, expressed on a particular cell located at a site of interest, etc. Numerous methods are well known in the art for engineering the cells, and may comprise the use of a vector, or naked DNA, wherein a nucleic acid coding for the targeting molecule of interest is introduced via any number of methods well described.

A nucleic acid sequence of interest may be subcloned within a particular vector, depending upon the desired method of introduction of the sequence within cells. Once the nucleic acid segment is subcloned into a particular vector it thereby becomes a recombinant vector. Polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides. Sequences of interest introduced as a nucleic acids such as DNA or RNA include the specific antigens and polypeptides comprising antigens for which the T regs of the invention are desiriously directed, as well as the sequence of TGF-$\beta$1 whose expression by dendritic cells is, in one embodiment, engineered hereby.

There are a number of techniques known in the art for introducing the above described recombinant vectors into cells, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation, liposome-mediated transfection, direct injection, and receptor-mediated uptake (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Bombardment with nucleic acid coated particles is also envisaged.

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product, which is easily detectable and, thus, can be used to evaluate efficacy of the system. Standard reporter genes used in the art include genes encoding β-galactosidase, chloramphenicol acetyl transferase, luciferase and human growth hormone, or any of the marker proteins listed herein.

In another embodiment, this invention provides a method for producing an isolated, culture-expanded T suppressor cell population, comprising contacting CD25− CD4+ T cells with dendritic cells and an antigenic peptide, and TGF-β1, for a period of time resulting in antigen-specific CD25+ CD4+ T cell expansion and optionally isolating the expanded CD25+ CD4+ T cells thus obtained, thereby producing a culture-expanded, antigen-specific T suppressor cell population.

In one embodiment, the term "dendritic cell" (DC) refers to antigen-presenting cells, which are capable of presenting antigen to T cells, in the context of MHC. In one embodiment, the dendritic cells utilized in the methods of this invention may be of any of several DC subsets, which differentiate from, in one embodiment, lymphoid or, in another embodiment, myeloid bone marrow progenitors. In one embodiment, DC development may be stimulated via the use of granulocyte-macrophage colony-stimulating-factor (GM-CSF), or in another embodiment, interleukin (IL)-3, which may, in another embodiment, enhance DC survival.

In another embodiment, DCs may be generated from proliferating progenitors isolated from bone marrow, as exemplified herein. In another embodiment, DCs may be isolated from CD34+ progenitors as described by Caux and Banchereau in Nature in 1992, or from monocytes, as described by Romani et al, J. Exp. Med. 180: 83-93 '94 and Bender et al, J. Immunol. Methods, 196: 121-135, '96 1996. In another embodiment, the DCs are isolated from blood, as described for example, in O'Doherty et al, J. Exp. Med. 178: 1067-1078 1993 and Immunology 82: 487-493 1994, all methods of which are incorporated fully herewith by reference.

In one embodiment, the DCs utilized in the methods of this invention may express myeloid markers, such as, for example, CD11c or, in another embodiment, an IL-3 receptor-α (IL-3Rα) chain (CD123). In another embodiment, the DCs may produce type I interferons (IFNs). In one embodiment, the DCs utilized in the methods of this invention express costimulatory molecules. In another embodiment, the DCs utilized in the methods of this invention may express additional adhesion molecules, which may, in one embodiment, serve as additional costimulatory molecules, or in another embodiment, serve to target the DCs to particular sites in vivo, when delivered via the methods of this invention, as described further hereinbelow.

In one embodiment, the DCs may be obtained from in vivo sources, such as, for example, most solid tissues in the body, peripheral blood, lymph nodes, gut associated lymphoid tissue, spleen, thymus, skin, sites of immunologic lesions, e.g. synovial fluid, pancreas, cerebrospinal fluid, tumor samples, granulomatous tissue, or any other source where such cells may be obtained. In one embodiment, the dendritic cells are obtained from human sources, which may be, in another embodiment, from human fetal, neonatal, child, or adult sources. In another embodiment, the dendritic cells used in the methods of this invention may be obtained from animal sources, such as, for example, porcine or simian, or any other animal of interest. In another embodiment, dendritic cells used in the methods of this invention may be obtained from subjects that are normal, or in another embodiment, diseased, or in another embodiment, susceptible to a disease of interest.

Dendritic cell separation may be accomplished in another embodiment, via any of the separation methods as described herein. In one embodiment, positive and/or negative affinity based selections are conducted. In one embodiment, positive selection is based on CD86 expression, and negative selection is based on GRI expression.

In another embodiment, the dendritic cells used in the methods of this invention may be generated in vitro by culturing monocytes in presence of GM-CSF and IL-4.

In one embodiment, the dendritic cells used in the methods of this invention may express CD83, an endocytic receptor to increase uptake of the autoantigen such as DEC-205/CD205 in one embodiment, or DC-LAMP (CD208) cell surface markers, or, in another embodiment, varying levels of the antigen presenting MHC class I and II products, or in another embodiment, accessory (adhesion and co-stimulatory) molecules including CD40, CD54, CD58 or CD86, or any combination thereof. In another embodiment, the dendritic cells may express varying levels of CD115, CD14, CD68 or CD32.

In one embodiment, mature dendritic cells are used for the methods of this invention. In one embodiment, the term "mature dendritic cells" refers to a population of dendritic cells with diminished CD115, CD14, CD68 or CD32 expression, or in another embodiment, a population of cells with enhanced CD86 expression, or a combination thereof. In another embodiment, mature dendritic cells will exhibit increased expression of one or more of p55, CD83, CD40 or CD86 or a combination thereof. In another embodiment, the dendritic cells used in the methods of this invention will express the DEC-205 receptor on their surface. In another embodiment, maturation of the DCs may be accomplished via, for example, CD40 ligation, CpG oligodeoxyribonucleotide addition, ligation of the IL-1, TNFα or TOLL like receptor ligand, bacterial lipoglycan or polysaccharide addition or activation of an intracellular pathway such as TRAF-6 or NF-κB.

In one embodiment, inducing DC maturation may be in combination with endocytic receptor delivery of a preselected antigen. In one embodiment, endocytic receptor delivery of antigen may be via the use of the DEC-205 receptor.

In one embodiment, the maturation status of the dendritic may be confirmed, for example, by detecting either one or more of 1) an increase expression of one or more of p55, CD83, CD40 or CD86 antigens; 2) loss of CD115, CD14, CD32 or CD68 antigen; or 3) reversion to a macrophage phenotype characterized by increased adhesion and loss of veils following the removal of cytokines which promote maturation of PBMCs to the immature dendritic cells, by methods well known in the art, such as, for example, immunohistochemistry, FACS analysis, and others.

Dendritic cells prepared from mice genetically deleted for CD80 and CD86 (B7-1 and B7-2) were demonstrated to be less efficient at stimulating proliferation of CD25+ CD4+ T cells (FIG. 4), playing a role in of CD25+ CD4+ T suppressor cell expansion. In one embodiment, the dendritic cells used for the methods of this invention may express, or in another embodiment, may be engineered to express a costimulatory molecule. In one embodiment, dendritic cells used for the methods of this invention are enriched for $CD86^{high}$ or $CD80^{high}$ expression.

In another embodiment, the dendritic cells used in the methods of this invention are selected for their capacity to expand antigen-specific CD25+CD4+ suppressor cells. In one embodiment, the DCs are isolated from progenitors or from blood for this purpose. In another embodiment, dendritic cells expressing high amounts of DEC-205/CD205 are used for this purpose.

T suppressor cell expansion, in one embodiment, is antigen-specific. In one embodiment, antigenic peptide or protein is supplied in the culture simultaneously with dendritic cell contact with CD25⁻ CD4⁺ cells. In another embodiment, dendritic cells, which have already processed antigen are contacted with the CD25⁻ CD4⁺ T cells.

In one embodiment, the term "contacting a target cell" refers herein to both direct and indirect exposure of cell to the indicated item. In one embodiment, contact of CD25⁻ CD4⁺ cells to an antigenic peptide, protein, cytokine, growth factor, dendritic cell, or combination thereof, is direct or indirect. In one embodiment, contacting a cell may comprise direct injection of the cell through any means well known in the art, such as microinjection. It is also envisaged, in another embodiment, that contacting or supplying to the cell is indirect, such as via provision in a culture medium that surrounds the cell, or administration to a subject, via any route well known in the art, and as described hereinbelow.

Methods for priming dendritic cells with antigen are well known to one skilled in the art, and may be effected, as described for example Hsu et al., Nature Med. 2:52-58 (1996); or Steinman et al. International application PCT/US93/03141. Antigens may, in one embodiment, be chosen for a particular application, or, in another embodiment, in accordance with the methods of this invention, as described further hereinbelow, and may be associated, in other embodiments, with fungal, bacterial, parasitic, viral, tumor, inflammatory, or autoimmune (i.e., self antigens) diseases.

In one embodiment, antigenic peptide or protein is added to a culture of dendritic cells prior to contact of the dendritic cells with CD 25⁻ CD4⁺ T cells. In one embodiment, soluble peptide or protein antigens are used at a concentration of between 10 pM to about 10 μM. In one embodiment, 30-100 ng ml⁻¹ is used. The dendritic cells are, in one embodiment, cultured in the presence of the antigen for a sufficient time to allow for uptake and presentation, prior to, or in another embodiment, concurrent with culture with CD25⁻ CD4⁺ T cells. In another embodiment, the antigenic peptide or protein is administered to the subject, and, in another embodiment, is targeted to the dendritic cell, wherein uptake occurs in vivo, for methods as described hereinbelow.

Antigenic protein or peptide uptake and processing, in one embodiment, can occur within 24 hours, or in another embodiment, longer periods of time may be necessary, such as, for example, up to and including 4 days or, in another embodiment, shorter periods of time may be necessary, such as, for example, about 1-2 hour periods.

In one embodiment, CD25⁻ CD4⁺ T cell expansion may be stimulated by a dendritic cell to T cell ratio of 1:1 to 1:10. In one embodiment, about 5 million T cells are administered to a subject.

In another embodiment, the CD25⁺ CD4⁺ T suppressor cells expanded by the methods of this invention are autologous, syngeneic or allogeneic, with respect to the dendritic cells. In another embodiment, the CD25⁺ CD4⁺ T suppressor cells expanded by the methods of this invention are enriched for CTLA-4high and/or GITRhigh expression. In another embodiment, the CD25⁺ CD4⁺ T suppressor cells expanded by the dendritic cells in the methods of this invention are engineered to express CTLA-4 and/or GITR.

In another embodiment, the dendritic cells used in the methods of this invention are isolated from a subject suffering from an autoimmune disease or disorder, and in another embodiment, the antigenic peptide or antigenic protein is associated with the autoimmune disease or disorder. The autoimmune disease or disorder may be any of those described hereinabove, such as for example type I diabetes, and in another embodiment, the antigenic peptide or protein may be expressed on pancreatic beta cells. In one embodiment, the antigenic peptide may be a BDC mimetope. In another embodiment, the antigenic peptide or protein may be derived insulin, proinsulin, preproinsulin, islet associated antigen (IAA), glutamic acid decarboxylase (GAD), or islet-specific glucose-6-phosphatase catalytic subunit related protein (IGRP). As described hereinabove, peptide libraries from these antigens or cells producing same may be utilized for any application in this invention.

In another embodiment, the dendritic cells used in the methods of this invention are isolated from a subject with an inappropriate or undesirable inflammatory response, and in another embodiment, the antigenic peptide or protein is associated with the inappropriate or undesirable inflammatory response.

In another embodiment, the dendritic cells used in the methods of this invention are isolated from a subject with an allergic response, and in another embodiment, the antigenic peptide or protein is associated with the allergic response.

In another embodiment, the dendritic cells used in the methods of this invention are isolated from a subject who is a recipient of a transplant. In one embodiment, the dendritic cells are isolated from a donor providing a transplant to said subject, and in another embodiment, the antigenic peptide or protein is associated with an immune response in the subject receiving a transplant from a donor.

In another embodiment, the immune response is a result of graft versus host disease. In another embodiment, the immune response is a result of host versus graft disease.

In another embodiment, the dendritic cells are engineered to express an antigen through introduction of a recombinant vector comprising nucleic acid encoding the antigen or encoding a polypeptide sequence comprising the antigen. Direct RNA transfection can also be used. Expression vectors prepared as described above and as generally known by the skilled artisan can be prepared and introduced into dendritic cells to provide the source of antigen as described herein. Thus, antigen comprising islet beta cell antigen, or antigen from, by way of example, rheumatoid arthritis, multiple sclerosis, myasthenia gravis, pernicious anemia, Addison's disease, lupus erythematosus, Reiter's syndrome, atopic dermatitis, psoriasis or Graves disease, are amenable to such methods.

Figure 1:
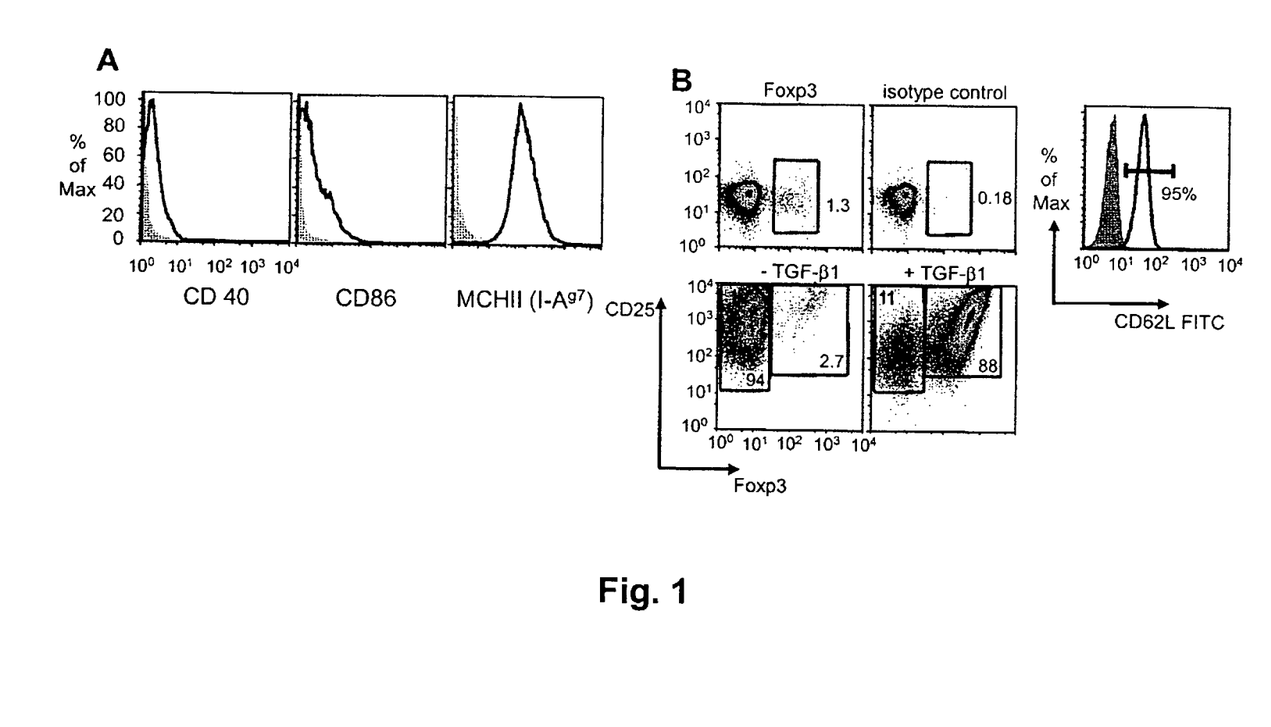

The source of TGF-β1 used in the practice of the embodiments herein may be provided by any number of sources. In one embodiment, naturally isolated or recombinant TGF-β1 can be used, such as recombinant human TGF-β1 purchased from R&D Systems. As shown in the examples herein, the induction of FoxP3⁺ cells by TGF-β1 was dose dependent, and was evident in vitro at 0.01 ng/ml and peaked at 1 ng/ml (FIG. 1D). One of skill in the art will readily determine the necessary amount of TGF-β1 to include in the particular embodiment of the invention being practiced, and adjust the amount accordingly. TGF-β1 can also be provided by including other TGF-β1-producing cells in the practice of the methods described herein, such as by including cells engineered to produce TGF-β1, whether by recombinant means or by induction to produce TGF-β1.

In yet another embodiment, dendritic cells can be engineered to express TGF-β1 by introducing therein an expression vector encoding TGF-β1. In another embodiment, dendritic cells can be induced to produce TGF-β1 or increased levels of TGF-β1 by, for example, contact with certain microbial products or cytokines. In another embodiment, as noted above, an expression vector encoding the desired antigen and in addition an expression vector encoding TGF-β1 can be introduced into dendritic cells to provide the requisite components along with the CD25⁻CD4⁺ cells to carry out the intended methods of the invention. In a further embodiment, a single expression vector comprising both antigen and TGF-β1 can be employed.

In one embodiment, the DC expanded CD25⁺ CD4⁺ T cells can be used to suppress an inflammatory response, in a disease-specific manner. In one embodiment, the T suppressor cells of this invention may suppress any autoimmune disease, allergic condition, transplant rejection, or chronic inflammation due to external causes, such as, for example inflammatory bowel disease. It is to be understood that any immune response, wherein it is desired to suppress such a response, the T suppressor cells of this invention may be thus utilized, and is an embodiment of this invention.

Thus, based on the teaching herein, an isolated, culture-expanded CD25⁺CD4⁺ T suppressor cell population is provided, wherein said population is prepared by the process of exposing CD25⁻ CD4⁺ T cells to dendritic cells, antigen and TGF-β1. The population can further express Foxp3 on its surface, among other markers. The population can be antigen specific. In certain embodiments, the dendritic cells exposed to the CD25⁻CD4⁺ T cells are presenting the antigen or a peptide thereof. As noted herein above, the antigen is a self-antigen, or a derivative thereof, such as a self antigen is expressed on pancreatic beta cells; alternately a mimetope such as BDC can be used.

In the embodiments in which suppression of a response to a transplant antigen is contemplated, the antigen can be a transplantation antigen.

A method is also provided for producing an isolated, culture-expanded CD25⁺CD4⁺ T suppressor cell population, comprising the steps of
  a. contacting a population of CD25⁻ CD4⁺ T cells with dendritic cells; an antigen selected from the group consisting of an antigenic peptide, an antigenic protein, and a derivative thereof; and TGF-β1, for a period of time resulting in antigen-specific CD25⁺ CD4⁺ T cell differentiation and expansion; and
  b. isolating the expanded CD25⁺ CD4⁺ T cells obtained in (a).

In the foregoing method, the CD25⁺CD4⁺ T suppressor cell population resulting from the methods herein can further express Foxp3 on its surface. The CD25⁺CD4⁺ T suppressor cell population can be antigen specific. The dendritic cells can present the antigen or a peptide thereof, and the antigen can be a self-antigen, or a derivative thereof. In one merely exemplary embodiment, the self antigen is expressed on pancreatic beta cells. In other embodiments, the antigen is a transplantation antigen. As noted above, the source of antigen, and independently, of TGF-β1, can be the dendritic cells, or other cell types, for this and other embodiments of the invention.

A method is provided for delaying the onset, reducing incidence, suppressing or treating autoimmunity, an autoimmune disease or an autoimmune disorder in a subject, comprising the steps of:
  a. contacting a population of CD25⁻ CD4⁺ T cells with dendritic cells; an antigen selected from the group consisting of an antigenic peptide, an antigenic protein, and a derivative thereof; and TGF-β1, for a period of time resulting in antigen-specific CD25⁺ CD4⁺ T cell differentiation and expansion; and
  b. administering the expanded CD25⁺ CD4⁺ T cells obtained in (a) to a subject.

In the practice of the aforementioned method, the autoimmune response can be directed towards rheumatoid arthritis or diabetes. In other embodiments, the method can be used to suppress an inflammatory response, or suppress an allergic response. In other embodiments it can be used to downmodulate an immune response. Non-limiting examples of such immune responses include graft versus host disease and host versus graft disease.

Similarly, a method is provided for downmodulating an immune response in a subject, comprising the steps of:
  a. contacting a population of CD25⁻ CD4⁺ T cells with dendritic cells; an antigen selected from the group consisting of an antigenic peptide, an antigenic protein, and a derivative thereof; and TGF-β1, for a period of time resulting in antigen-specific CD25⁺ CD4⁺ T cell differentiation and expansion; and
  b. administering the expanded CD25⁺ CD4⁺ T cells obtained in (a) to a subject.

In one embodiment, cells for administration to a subject in this invention may be provided in a composition. These compositions may, in one embodiment, be administered parenterally or intravenously. The compositions for administration may be, in one embodiment, sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium. In another embodiment, the compositions may comprise adjuvants, which are well known to a person skilled in the art (for example, vitamin C, antioxidant agents, etc.) for some of the methods as described herein, wherein stimulation of an immune response is desired, as described further hereinbelow.

In one embodiment, the cells or compositions of this invention may be administered to a subject via injection. In one embodiment, injection may be via any means known in the art, and may include, for example, intra-lymphoidal, or subcutaneous injection.

In another embodiment, the T suppressor cells and dendritic cells for administration in this invention may express adhesion molecules for targeting to particular sites. In one embodiment, T suppressor cell and/or dendritic cells may be engineered to express desired molecules, or, in another embodiment, may be stimulated to express the same. In one embodiment, the DC cells for administration in this invention may further express chemokine receptors, in addition to adhesion molecules, and in another embodiment, expression of the same may serve to attract the DC to secondary lymphoid organs for priming. In another embodiment, targeting of DCs to these sites may be accomplished via injecting the DCs directly to secondary lymphoid organs through intralymphatic or intranodal injection.

In one embodiment, the antigen is delivered to dendritic cells in vivo in the steady state, which, in another embodiment, leads to expansion of disease specific suppressors. Antigen delivery in the steady state can be accomplished, in one embodiment, as described (Bonifaz, et al. (2002) Journal of Experimental Medicine 196: 1627-1638; Manavalan et al. (2003) Transpl Immunol. 11: 245-58).

In one embodiment, the antigens are targeted to dendritic cells in vivo to modulate suppressor cells as described herein. In one embodiment, antigens are targeted to subsets of dendritic cells, which expand suppressors in vivo. In one embodiment, the antigen may be genetically engineered, for example, and in another embodiment, an islet cell autoantigen is engineered to be expressed as a fusion protein, with an antibody that targets dendritic cells, such as, for example, the DEC-205 antibody. Methods for accomplishing this are known in the art, and may be, for example, as described, Hawiger D. et al. J. Exp. Med., Volume 194, (2001) 769-780.

In another embodiment, select types of dendritic cells in vivo function to expand the T suppressor cells. In one embodiment, the use of dendritic cells and a single antigen, will block a disease, which is caused by an autoimmune response directed to multiple antigens.

In one embodiment, the suppressor T cells of this invention may be administered to a recipient contemporaneously with a graft or transplant. In another embodiment, the suppressor T cells of this invention may be administered prior to the administration of the transplant. In one embodiment, the suppressor T cells of this invention may be administered to the recipient about 3 to 7 days before transplantation of the donor tissue. The dosage of the suppressor T cells varies within wide limits and will, of course be fitted to the individual requirements in each particular case, and may be, in another embodiment, a reflection of the weight and condition of the recipient, the number of or frequency of administrations, and other variables known to those of skill in the art. The suppressor T cells can be administered, in other embodiments, by a route, which is suitable for the tissue, organ or cells to be transplanted. The T suppressor cells of this invention may be administered systemically, i.e., parenterally, by intravenous injection or targeted to a particular tissue or organ, such as bone marrow. The suppressor T cells of this invention may, in another embodiment, be administered via a subcutaneous implantation of cells or by injection of stem cell into connective tissue, for example muscle.

In one embodiment, the term "downmodulating" refers to inhibition, suppression or prevention of a particular immune response. In one embodiment, downmodulating results in diminished cytokine expression, which provides for diminished immune responses, or their prevention. In another embodiment, downmodulation results in the production of specific cytokines which have a suppressive activity on immune responses, or, in another embodiment, inflammatory responses in particular.

The following non-limiting examples may help to illustrate some embodiments of the invention.

EXAMPLES

Materials and Methods

Mice. NOD, NOD.scid, and BDC2.5 TCR transgenic mice were purchased from The Jackson Laboratory (West Grove, Pa.). Mice were used according to institutional guidelines and protocols approved by the institutional Animal Care and Use Committees at Northwestern University, Cornell University, and The Rockefeller University.

Antibodies. Biotinylated mAbs for CD8 (53-6.7), CD25 (7D4), Ly-76 (Ter-119), Grl (RB6-8C5), CD49b/Pan-NK (DX5), B220 (RA3-682), and CD11b (M1/70); FITC-conjugated anti-CD4 (GK1.5), CD11c (HL3), I-A$^{g7}$ (OX-6); PE-conjugated anti-IL-17 (TC11-18H10), IL-10 (JES5-16E3), CD25 (PC61), CD86 (GL1), GITR (DTA-1); and APC-conjugated anti-CD62L (MEL-14) were from BD Biosciences (Franklin Lakes, N.J.). PE-conjugated anti-CD152 (UC10-4B9) and Foxp3 (FJK-16s) in addition to APC-conjugated anti-CD25 (PC61) were from eBioscience (San Diego, Calif.). A hybridoma expressing the anti-clonotype antibody that is specific for BDC2.5 TCR (BDC) was provided by O. Kanagawa (Washington University, St. Louis, Mo.), and the antibody was purified and biotinylated. Recombinant human TGF-β1 was obtained from R&D Systems, (Minneapolis, Minn.).

Cell Purifications. Splenic DCs were isolated from NOD males as described in ref. 36. In brief, spleens from normoglycemic NOD males between the ages of 4 and 10 weeks were first digested with collagenase D (Sigma-Aldrich, St. Louis, Mo.) followed by the enrichment of the DC fraction with 30% BSA density gradient. The CD11c fraction was then purified with magnetic microbeads (Miltenyi Biotec, Auburn, Calif.). The purity of DCs was routinely >90%. DCs were irradiated with 15 Gy before their use as APCs. Naïve CD4$^+$CD25$^-$ cells were purified from BDC2.5 spleen and lymph nodes. Cells were first enriched by depletion (anti-CD8, CD25, Ter119, Grl, DX5, B220, CD11b) followed by FACS sorting for the CD4$^+$CD25$^-$CD62L$^+$ population to >95% purity.

Cell Culture, Proliferation Assays, and Cytokine Detection. The sequence of the mimetope peptide used (BDC) was RVRPLWVRME (SEQ ID NO: 4.) A total of 2×10$^4$ per well of CD4$^+$ CD25$^-$ BDC2.5 T cells were cultured for 6-10 days with splenic DCs at a 3:1 T/DC cell ratio in 96-well plates with 100 ng/ml BDC peptide, either with or without TGF-β1 at indicated concentrations. Alternatively, T cells were cultured with 10 µg/ml anti-CD3 (a gift from Terrence Barrett, San Jose, Calif.) and 2 µg/ml anti-CD28 (BD Biosciences, San Jose, Calif.) for 6 days. For functional tests, DCs were removed by CD11c antibody-conjugated magnetic microbeads, and CD25$^+$ cells were further enriched by labeling them with PE-conjugated anti-CD25 (PC61) and anti-PE microbeads. For proliferation assays, freshly isolated CD4$^+$ CD25$^-$ BDC2.5 T cells were cultured with NOD whole spleen cells at a T/APC cell ratio of 1:5 and 100 ng/ml BDC peptide. [$^3$H]thymidine (1 µCi per well; PerkinElmer, San Jose, Calif.) was added for the last 18 h of a 72-h assay. For suppression assays, the cultured CD25$^+$T cells were added to proliferation assays at the indicated ratios and [$^3$H]thymidine uptake was measured. For cytokine assays, culture supernatants were tested with the LiquiChip Mouse 10-cytokine assay kit (Qiagen, Valencia, Calif.). For intracellular cytokine detection, cells were first stimulated with leukocyte activation mixture (BD Biosciences) for 4 h before being stained in accordance with the manufacturer's protocol.

Real-Time PCR. Total RNA was extracted with the RNeasy mini kit (Qiagen). The sequences of primers and probe for mouse Foxp3 were as follows: sense 5'-AGGAGAAGCTGG-GAGCTATGC-3' (SEQ ID NO: 1); anti-sense 5'-TGGCTAC-GATGCAGCAA GAG-3' (SEQ ID NO:2); probe 5'-FAM AGCGCCATCTTCCCAGCCAGG TAMRA-3' (SEQ ID NO:3). The final quantity of mRNA was calculated as copies per microgram of RNA and standardized according to 18s RNA.

Diabetes Experiments. For NOD.scid experiment, diabetes was induced in 5- to 9-week-old NOD.scid mice with an i.v. injection of 10$^7$ spleen cells from female NOD mice with diabetes. Indicated numbers of the induced CD4$^+$CD25$^+$ T cells were coinjected where indicated. Urine glucose was checked two to three times per week, and the development of diabetes in NOD.scid mice was defined as three consecutive positive urine glucose readings.

The spontaneous development of diabetes in female NOD mice was defined as two consecutive blood glucose levels of >250 mg/dl. Islet isolation and transplantation were performed as described in ref. 22. In brief, islets were hand-picked to a purity of >80% for transplant, and 500-600 islets were transplanted into the kidney subcapsular space of newly diabetic NOD female mice. For cell and islet cotransplants, the indicated numbers of T cells were mixed with islets immediately before transplantation. Graft destruction was diagnosed by the recurrence of hyperglycemia (blood glucose level >250 mg/dl on two consecutive readings).

Statistical Analysis. For analysis of real-time PCR data, we used the Student's t test. To analyze the incidence of diabetes in NOD.scid and syngeneic islet graft survival in NOD recipients, we used analysis of variance. P<0.05 was considered to be significant.

Example 1

Splenic CD11c$^+$ DCs Induce Differentiation of CD4$^+$ CD25$^+$Foxp3$^+$ T Regs from CD4$^+$CD25$^-$ T Cells in the Presence of TGF-$\beta$1.

To test the role of DCs in the de novo differentiation of CD4$^+$CD25$^+$Foxp3$^+$ T regs, CD4$^+$CD25$^-$ T cells were used from the BDC2.5 TCR transgenic NOD mice. These T cells respond to both an unidentified autoantigen expressed in the secretory granules of islet $\beta$cells and a mimetope peptide (BDC). CD11c$^+$ DCs were isolated from splenocytes of NOD mice and characterized for expression of CD40, CD86, and MHCII (FIG. 1A). Compared with LPS-matured DCs, these freshly isolated DCs express weaker CD40 and MHC II and significantly less CD86 (data not shown), suggesting a relatively immature phenotype. A starting population of CD4$^+$CD25$^-$CD62L$^+$ BDC2.5 T cells was also characterized, after FACS sorting to a purity of >95%, and found the expected small fraction of Foxp3$^+$ cells (FIG. 1B). DCs were then added together with the BDC peptide to the CD4$^+$CD25$^-$ BDC2.5 T cells in the presence or absence of TGF-01. After 6 days of culture, good induction of Foxp3 mRNA (FIG. 1D) and protein (FIG. 1B) were observed, but only when TGF-$\beta$1 was included in the cultures. In the presence of TGF-$\beta$1, the frequency of Foxp3$^+$ cells increased to 88.3±7% (n=3; FIG. 1B), and their numbers increased ≈50- to 100-fold (FIG. 1C). The newly formed Foxp3$^+$ cells appeared by 2 days of culture, and the total number of Foxp3$^+$ cells peaked at 4 days and decreased after 6 days. Because of the rapid appearance of the Foxp3$^+$ cells, the increase observed is unlikely to be caused by the expansion of the few Foxp3$^+$ cells in the starting population. In the absence of TGF-$\beta$1, the percentage of Foxp3$^+$ cells remained close to baseline, although CD25 expression was still induced (FIG. 1B). Quantification of Foxp3 mRNA expression by real-time RT-PCR demonstrated that the level induced by the DCs and TGF-$\beta$1 was equivalent to that found in naturally occurring T regs (FIG. 1D). The induction of Foxp3$^+$ cells by TGF-1 was dose-dependent, being readily evident at 0.01 ng/ml and peaking at 1 ng/ml (FIG. 1E). Therefore, DCs can serve as effective APCs for differentiating Foxp3$^+$ T cells from CD4$^+$CD25$^-$Foxp3$^-$ precursors in the presence of low-dose TGF-$\beta$1.

Example 2

Characterization of CD4$^+$CD25$^+$Foxp3$^+$ T Regs Induced by DCs and TGF-$\beta$1

Figure 2:
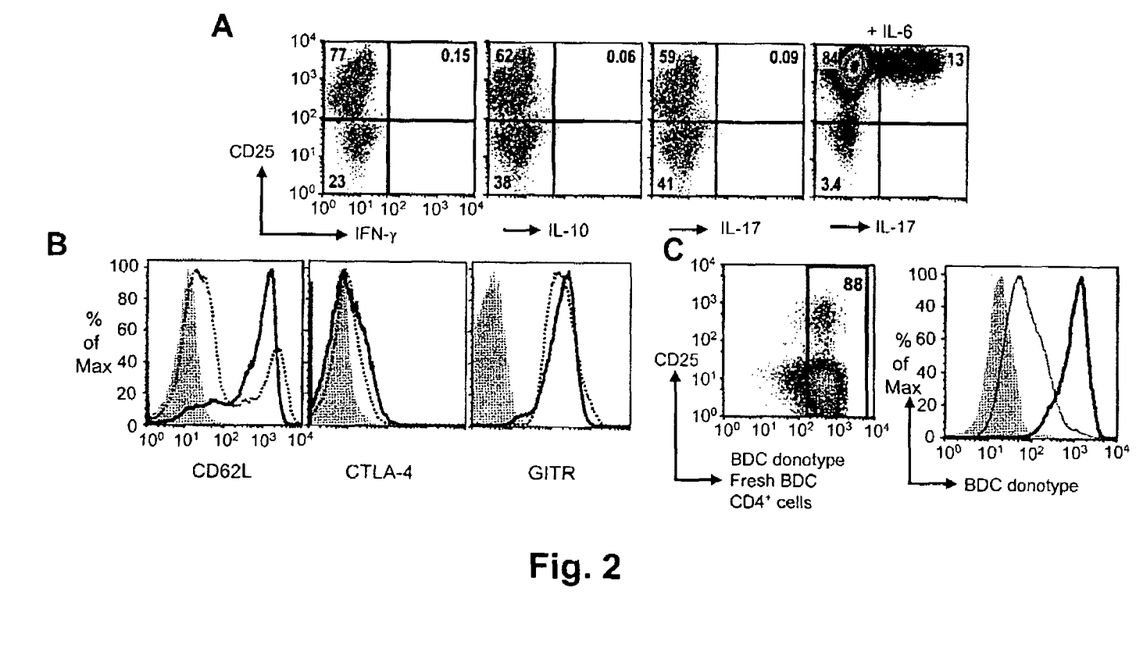
FIG. 2 shows the characterization of CD4$^+$CD25$^+$Foxp3$^+$ BDC T cells induced by DCs and TGF-β1. (A) Intracellular expressions of IFN-γ, IL-10, and IL-17 on day 6 of DC-T coculture. The addition of 20 ng/ml IL-6 induced L-17 expression. (B) Expression of CD62L, CTLA-4, and GITR on day 6 of DC-T coculture. Cells cultured in the absence of TGF-β1 were also shown for comparison. Shaded histogram, isotype control; solid line, +TGF-β1; dotted line, −TGF-β1. (C) BDC clonotype expression. (Left) Freshly isolated BDC2.5 CD4$^+$ T cells. (Right) T cells on day 6 after culture. Shaded histogram, isotype control; thick line, T cells cultured with DCs and TGF-β1; thin line, T cells cultured with anti-CD3, anti-CD28, and TGF-β1. All results are representative of two to four separate experiments.

Cytokine expression by T cells cultured with splenic DCs and TGF-1 was determined. No IFN-$\gamma$ or IL-10 was observed (FIG. 2A). Because TGF-$\beta$1 is able to induce IL-17-secreting cells or Foxp3$^+$ cells depending on the presence or absence of IL-6, IL-17 production was also tested. T cells cultured with splenic DCs and TGF-$\beta$1 were negative for IL-17 expression, whereas as a positive control, T cells cultured with IL-6 and TGF-$\beta$1 did express IL-17 (FIG. 2A).

Next, expression was measured of proteins associated with T reg function in the CD4$^+$CD25$^+$Foxp3$^+$ T cells differentiated by splenic DCs and TGF-$\beta$1. As shown in FIG. 2B, a greater percentage of T cells cultured in the presence of TGF-$\beta$1 retained CD62L expression compared with those cultured in the absence of TGF-$\beta$1. T cells cultured either with or without TGF-$\beta$1 up-regulated both CTLA-4 and glucocorticoid-induced TNF receptor (GITR; FIG. 2B), whereas freshly purified T cells were negative for both (data not shown).

Because the level of TCR expression contributes to the avidity of T cell responses, BDC clonotype expression was measured before and after stimulation. Approximately 90% of freshly isolated CD4$^+$ BDC2.5 T cells were clonotype$^+$ (FIG. 2C). Stimulation with splenic DCs pulsed with the BDC peptide maintained high levels of clonotype expression. In contrast, nonspecific stimulation with anti-CD3/CD28 resulted in much lower clonotype expression (FIG. 2C). These observations indicate that the DC and TGF-$\beta$1-induced T regs share many features with natural T regs.

Example 3

In Vitro Suppression of CD4$^+$CD25$^+$Foxp3$^+$ T Regs Induced by DCs and TGF-$\beta$1

Figure 3:
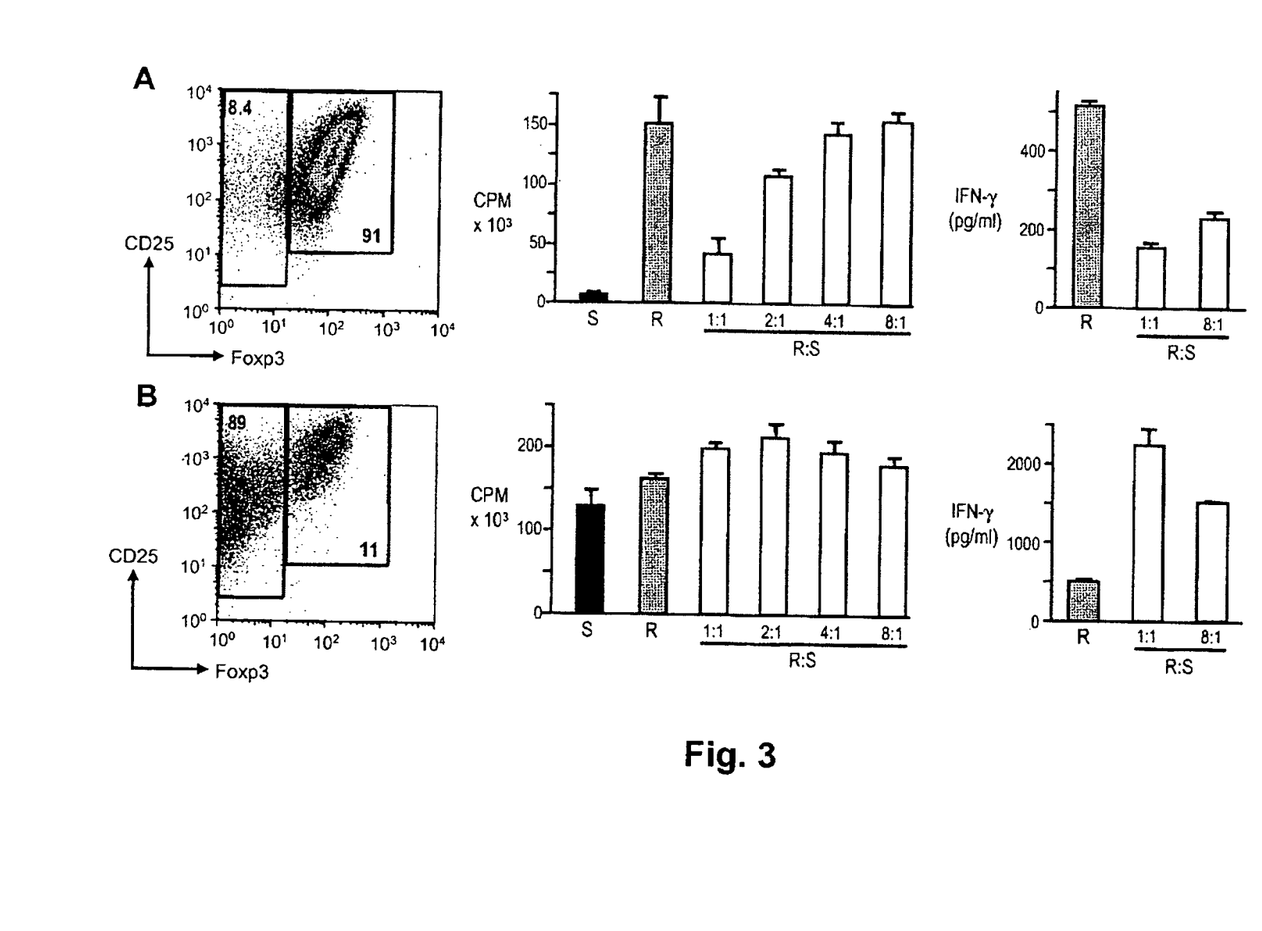
FIG. 3 shows that CD4$^+$CD25$^+$Foxp3$^+$ BDC T cells induced by DCs and TGF-β1 suppress BDC-specific T cell proliferation and cytokine production. After 6 days of culture with (A) or without (B) TGF-β1, CD11c$^+$ cells were depleted and CD25$^+$ cells were enriched. FACS plots constructed after the enrichment are shown (Left). Proliferation assays were set up with CD4$^+$CD25$^-$ cells from BDC2.5 mice [responders (R)], APCs from NOD mice, and BDC peptide (100 ng/ml). Increasing numbers of the induced CD4$^+$CD25$^+$ cells [suppressors (S)] were added at ratios indicated. Proliferation was assessed by [$^3$H]thymidine uptake (Center), and IFN-γ was measured from culture supernatants (Right) as described in Materials and Methods.

To test for the suppressive function of the CD4$^+$CD25$^+$Foxp3$^+$ T cells induced with splenic DCs and TGF-$\beta$1, an in vitro assay was used first. CD11c$^+$ cells were depleted and CD25$^+$ T cell fraction enriched from 6-day cultures with DCs and the resulting CD4$^+$CD25$^+$ T cells added in graded doses to responder CD4$^+$CD25$^-$ BDC2.5 T cells. Inhibition of proliferation was measured to BDC peptide presented by whole NOD splenic APCs. As shown in FIG. 3A, in the presence of TGF-$\beta$1, the DC-induced CD4$^+$CD25$^+$ T cells were 91% Foxp3$^+$ after enrichment. They were anergic in response to BDC peptide and were able to block the proliferation of naïve BDC2.5 T cells to BDC peptide (70% suppression at a 1:1 ratio). This ratio of T regs needed for suppression was greater than required for DC-expanded natural T regs, which gave similar suppression of proliferation with 4-fold fewer T regs. Suppression of IFN-$\gamma$ secretion was also observed and at a responder/suppressor ratio as low as 8:1 (FIG. 3A). In contrast, in the absence of TGF-$\beta$1, the resulting CD4$^+$CD25$^+$ T cells were only 11% Foxp3$^+$ after enrichment. They showed vigorous proliferation to BDC peptide themselves, were unable to suppress proliferation of naïve BDC2.5 T cells, and led to augmented IFN-$\gamma$ secretion (FIG. 3B). Therefore, the induced Foxp3$^+$ T regs have some suppressive function in vitro, although they are less potent than natural T regs after expansion with DCs.

Example 4

CD4$^+$CD25$^+$Foxp3$^+$ T Regs Induced by DCs and TGF-$\beta$1 Suppress Autoimmune Diabetes in Vivo A more critical function for naturally occurring CD4$^+$CD25$^+$ T regs is the suppression of autoimmunity in vivo. To test whether the T regs induced by splenic DCs and TGF-$\beta$1 could inhibit autoimmune diabetes, adoptive transfer was first used in NOD.scid recipients. In this model, injection of diabetogenic splenocytes from acutely diabetic NOD mice into NOD.scid recipients results in rapid autoimmune destruction of the native pancreas and consequent development of hyperglycemia. Because a known quantity of diabetogenic splenocytes is injected into the NOD.scid recipients, this model allows for a measurement of the potency of the DC-induced T regs according to the kinetics of diabetes development after injection. As shown in FIG. 4, i.v. coinjection of $3 \times 10^5$ of the DC+ TGF-β1-induced CD4$^+$CD25$^+$ T cells along with $10^7$ diabetogenic splenocytes resulted in complete protection from the development of diabetes (0/6 recipients developed diabetes at 120 days after injection). In addition, 10-fold fewer ($3 \times 10^4$) of the same T cells coinjected with $10^7$ diabetogenic splenocytes still resulted in a significant delay of onset and a lower incidence of diabetes. In contrast, injection of either dose of the CD4$^+$CD25$^+$ T cells from cultures without TGF-β1 along with $10^7$ diabetogenic splenocytes resulted in accelerated onset of diabetes in NOD.scid recipients.

Next, the efficacy of these T regs was tested in blocking autoimmune destruction of a syngeneic islet graft in spontaneously diabetic NOD recipients. This model represents a clinically relevant scenario of diabetes pathogenesis in which islet-specific effector cells are already present in a nonlymphopoenic host. Without intervention, ongoing autoimmunity directed toward the transplanted islet β cells results in graft destruction within 5-17 days after transplantation. To avoid the confounding factor of T reg cell trafficking, the T regs were directly deposited at the site of the islet graft, i.e., the kidney subcapsular space. When $3 \times 10^5$ DC+ TGF-β1-induced CD4$^+$CD25$^+$ T cells along with the syngeneic islets were cotransplanted into the kidney subcapsular space of diabetic NOD recipients, there was a significant prolongation of graft survival (FIG. 5). In contrast, CD4$^+$CD25$^+$ T cells induced in the absence of TGF-β1-accelerated isograft destruction.

Thus, in both the adoptive transfer NOD.scid model and the spontaneous diabetes NOD model, the CD4$^+$CD25$^+$ Foxp3$^+$ T regs induced by DCs and TGF-β1 were able to effectively block autoimmunity mediated by a diverse repertoire of autoreactive TCR specificities, analogous to the previously reported properties of "natural" T regs.

What is claimed is:

1. A method for producing an isolated, antigen specific culture-expanded CD25$^+$CD4$^+$ T suppressor cell population, comprising:
   a) purifying a population of CD25$^-$CD4$^+$ T cells;
   b) purifying a greater than 90% population of immature dendritic cells;
   c) contacting the population of CD25$^-$CD4$^+$ T cells with the immature dendritic cells; an antigen selected from the group consisting of an antigenic peptide or an antigenic protein; and TGF-β1, for a period of time resulting in antigen-specific CD25$^+$CD4$^+$ T cell differentiation and expansion, wherein the ratio of the immature dendritic cells to the CD25$^-$CD4$^+$ T cells is between 1:1 and 1:10 and the concentration of the antigen is 30-100 ng/ml; and
   d) isolating the expanded CD25$^+$CD4$^+$ T cells obtained in (c),
   thereby producing an isolated, antigen specific culture-expanded CD25$^+$CD4$^+$ T suppressor cell population with an in vivo immune suppressive activity, wherein the CD25$^+$CD4$^+$ T suppressor cell population do not express IL-10.

2. The method of claim 1, wherein said isolated, antigen specific culture-expanded CD25$^+$CD25$^+$ T suppressor cell population further expresses Foxp3.

3. The method of claim 1, wherein the dendritic cells are presenting the antigen or a peptide thereof, or are engineered to express the antigen or a peptide thereof.

4. The method of claim 1, wherein the antigen is a pancreatic beta cell antigen, a transplantation antigen, or a rheumatoid arthritis antigen.

5. The method of claim 1, wherein said population suppresses or down modulates an inflammatory response, an allergic response, or an immune response.

6. The method of claim 5, wherein said immune response is graft versus host disease or host versus graft disease.

7. The method of claim 1, wherein the TGF-β1 is exogenous or expressed by the dendritic cells or other cells.

8. The method of claim 1, wherein said dendritic cells are isolated from a subject suffering from an autoimmune disease or disorder.

9. The method of claim 8, wherein said antigenic peptide or antigenic protein is associated with said autoimmune disease or disorder.

10. The method of claim 9, wherein said autoimmune disease or disorder is type I diabetes, graft-vs.-host disease or host-vs.-graft disease.

11. The method of claim 9, wherein said antigenic peptide or protein is expressed in pancreatic beta cells.

12. The method of claim 11 wherein said antigenic peptide is a BDC mimetope.

13. The method of claim 2, wherein said dendritic cells are isolated from a subject with an allergic response, a recipient of a transplant, or a donor providing a transplant to said subject.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: Mus musculus

<400> SEQUENCE: 1
aggagaagct gggagctatg c                                              21

<210> SEQ ID NO 2
<211> LENGTH: 20
<212> TYPE: DNA
<213> ORGANISM: Artificial
<220> FEATURE:
<223> OTHER INFORMATION: Mus musculus

<400> SEQUENCE: 2
tggctacgat gcagcaagag                                                20

<210> SEQ ID NO 3
<211> LENGTH: 21
<212> TYPE: DNA
<213> ORGANISM: Artificial
<220> FEATURE:
<223> OTHER INFORMATION: Mus musculus

<400> SEQUENCE: 3
agcgccatct tcccagccag g                                              21

<210> SEQ ID NO 4
<211> LENGTH: 10
<212> TYPE: PRT
<213> ORGANISM: Artificial
<220> FEATURE:
<223> OTHER INFORMATION: mimetope peptide

<400> SEQUENCE: 4

Arg Val Arg Pro Leu Trp Val Arg Met Glu
1               5                   10